United States Patent [19]

Roschger et al.

[11] Patent Number: 5,621,027
[45] Date of Patent: Apr. 15, 1997

[54] DYESTUFFS FOR BULK DYEING PLASTICS

[75] Inventors: Peter Roschger; Volker Hederich, both of Köln; Stephan Michaelis, Leverkusen; Friedrich W. Kröck, Odenthal, all of Germany

[73] Assignee: Bayer Aktiengesellschaft, Leverkusen, Germany

[21] Appl. No.: 439,809

[22] Filed: May 12, 1995

[30] Foreign Application Priority Data

May 20, 1994 [DE] Germany .................. 44 17 746.1

[51] Int. Cl.$^6$ .................. C08K 5/34; C07D 239/70; C09B 57/12
[52] U.S. Cl. .................. 524/90; 8/506; 8/508; 8/512; 544/245
[58] Field of Search .................. 8/506, 508, 512; 524/90; 544/245

[56] References Cited

U.S. PATENT DOCUMENTS

| | | | |
|---|---|---|---|
| 4,417,014 | 11/1983 | Buecheler | 544/245 |
| 5,466,805 | 11/1995 | Roschger | 544/245 |

FOREIGN PATENT DOCUMENTS

| | | |
|---|---|---|
| 0570800 | 11/1993 | European Pat. Off. . |
| 1075110 | 10/1954 | France . |
| 1108109 | 1/1956 | France . |
| 1166701 | 11/1958 | France . |
| 2053069 | 2/1990 | Japan . |

OTHER PUBLICATIONS

JP06502425–W, p. 12, (Mar. 17, 1994).
Sachs, Liebigs Ann. Chem., vol. 365, pp. 126–131 (1909).
English Abstract of JP 49–009,552 (1974).
English Abstract of JP 49–009 530 (1972).
DRP 202 354 (Sep. 1908).
G. Wanag, Chem. Ber. vol. 75, pp. 719–725 (1942).
O. Mumm et al., Chem Ber., 50, pp. 1568–1584 (1917).

*Primary Examiner*—Kriellion S. Morgan
*Attorney, Agent, or Firm*—Sprung Horn Kramer & Woods

[57] ABSTRACT

Dyestuffs of the formula

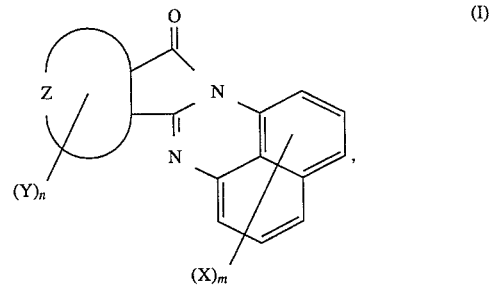

wherein
Z denotes a radical to complete a 3,4- or 2,3-pyridinylene, a 4,5-pyrimidinylene, a 3,4- or 4,5-pyridazinylene or a 2,3-pyrazinylene system and
X, Y, m and n have the meanings given in the description, which are particularly suitable for bulk dyeing plastics, in particular thermoplastics, have been found.

10 Claims, No Drawings

DYESTUFFS FOR BULK DYEING PLASTICS

The invention relates to dyestuffs, a process for their preparation and their use for bulk dyeing plastics.

Dyestuffs such as are described, for example, in JP-A-4 909 530, JP-A-4 909 552, FR 1.166.701 and FR 1.075.110 are known for dyeing plastics, but have certain disadvantages in respect of their fastness properties.

Azaphthaloperinone dyestuffs of the general formula (I)

(I)

wherein

Z denotes a radical to complete a 3,4- or 2,3-pyridinylene, a 4,5-pyrimidinylene, a 3,4- or 4,5-pyridazinylene or a 2,3-pyrazinylene system, X is alkyl, halogen, nitro, chlorosulphonyl, aryloxy-sulphonyl, hydroxyl, alkoxy, acyloxy, an amino-sulphonyl which is optionally substituted by alkyl or aryl, or a fused-on cycloaliphatic or heterocyclic ring, Y is alkyl, aryl, halogen, nitro, hydroxyl, alkoxy, acyloxy, in particular chlorosulphonyl, aryloxysulphonyl, an amino group which is optionally substituted by acyl or alkyl, an aminosulphonyl radical which is optionally substituted by alkyl or aryl, or a fused-on cycloaliphatic or aromatic ring, m is a number between 0 and 6, n is a number between 0 and 3 and for m>1

X can in each case have different or identical meanings as mentioned above, and for n>1

Y can in each case have different or identical meanings as mentioned above, have now been found.

Alkyl or alkoxy is preferably understood as meaning $C_1$–$C_{18}$-alkyl, in particular $C_1$–$C_6$-alkyl, or -alkoxy, and aryl is preferably understood as meaning $C_6$–$C_{14}$, in particular $C_6$–$C_{10}$; halogen is preferably understood as meaning Cl, Br or F, and acyl is preferably understood as meaning $C_1$$_4$–$C_{18}$-, in particular $C_1$–$C_6$-alkylcarbonyl or -sulphonyl or $C_6$–$C_{14}$-, in particular $C_6$–$C_{10}$-arylcarbonyl or -sulphonyl.

Preferred dyestuffs of the formula I are those wherein

Z denotes a radical to complete a 3,4-pyridinylene system.

In a particular embodiment

X denotes chlorine, bromine, -$NO_2$, -$OCH_3$, -$OCH_2(C_6H_5)$, chlorosulphonyl, -OH, -$SO_2O(C_6H_5)$, -$SO_2N(CH_3)_2$, -$SO_2NHCH_3$, methyl, ethyl, n-propyl, isopropyl, n-butyl, iso-butyl, sec-butyl, tert-butyl or a cycloaliphatic 5- or 6-membered ring which is preferably fused on in the 4,5-position, wherein -$C_6H_5$ here and also in the following represents phenyl, Y denotes methyl, ethyl, n-propyl, isopropyl, n-butyl, iso-butyl, sec-butyl, tert-butyl, a phenyl which is optionally substituted by $C_1$–$C_6$-alkoxy, $C_1$–$C_6$-alkyl, Cl, Br or F, a fused-on cycloaliphatic 5-, 6- or 7-membered ring or a fused-on benzo ring, which is optionally substituted by Cl, Br, $C_1$–$C_4$-alkyl or $C_1$–$C_4$-alkoxy, m denotes a number between 0 and 4 and n denotes a number between 0 and 3.

In an especially preferred embodiment, m denotes 0.

The general formula (I) of the dyestuffs according-to the invention is understood as meaning either isomerically pure compounds or mixtures thereof. Preferred dyestuffs of the formula (I) correspond to the formulae Ia and Ib.

(Ia)

(Ib)

The indices n and m here can have the character of a statistical figure and can thus assume any desired number in the range defined.

The dyestuffs of the formula (I) according to the invention can be prepared by processes which are known per se (cf., for example, DRP 202 354, Chem. Bet. 75 (1942), 719; Liebigs Ann. Chem. 365 (1909), 128) by condensation of dicarboxylic acids or functional derivatives thereof of the formula (II)

(II)

wherein Z, Y and n have the above meanings, with naphthalene-1,8-diamines of the formula (III)

(III)

in which X and m have the meanings given.

Dicarboxylic acids or functional derivatives thereof of the formula (IIa)–(IIf)

(IIa)

(IIb)

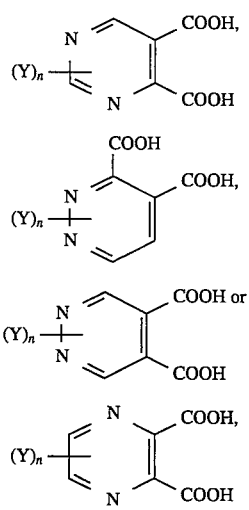

wherein Y and n have the meanings given, are employed in particular in this process.

The use of dicarboxylic acids of the formula (IIa) or functional derivatives thereof, in particular anhydrides thereof, is particularly preferred. Preferred functional derivatives of the dicarboxylic acids are their anhydrides.

The condensation reaction can be carried out here directly by fusing equimolar amounts of the components of the formulae (II) and (III) together at temperatures of between 50° C. and 220° C., preferably at 120° to 180° C., or more advantageously in a solvent at temperatures of between 20° C. and 220° C., preferably 50° to 180° C., if appropriate under pressure, it being possible for the water of reaction to be removed by distillation.

Suitable solvents are, for example: chlorobenzene, o-dichlorobenzene, trichlorobenzene, xylene, dimethylformamide, N-methylpyrrolidone, glacial acetic acid, propionic acid, phenol, cresols, phenoxyethanol, glycols and mono- and dialkylethers thereof, alcohols, for example methanol, ethanol and i-propanol, water and aqueous solvents, such as, for example, dilute sulphuric acid and the like.

If appropriate, the reaction can be carried out with addition of an acid catalyst.

Suitable catalysts are, for example: zinc chloride, p-toluenesulphonic acid, hydrochloric acid, sulphuric acid, organic acids and the like.

The corresponding pyridine-3,4-dicarboxylic acids (or functional derivatives thereof) are commercially obtainable or can be prepared, for example, in accordance with Chem. Bet. 50, pp. 1568–1584 (1917). Suitable pyridinedicarboxylic acids are, for example:

pyridine-3,4-dicarboxylic acid, 2,6-dimethylpyridine-3,4-dicarboxylic acid, 2,5,6-trimethylpyridine-3,4-dicarboxylic acid, 6-phenyl-pyridine-3,4-dicarboxylic acid, 6-phenyl-2-methyl-pyridine-3,4-dicarboxylic acid, 5,6-tetramethylene-pyridine-3,4-dicarboxylic acid, 5,6-trimethylene-pyridine-3,4-dicarboxylic acid, 6-(4-chlorophenyl)pyridine-3,4-dicarboxylic acid, 6-(2,4-dichlorophenyl)-2-methyl-pyridine-3,4-dicarboxylic acid, 2,6-diphenyl-pyridine-3,4-dicarboxylic acid, 5,6-diphenyl-pyridine-3,4-dicarboxylic acid, 2,6-diethyl-pyridine-3,4-dicarboxylic acid, 2-ethyl-5-methyl-6-phenyl-pyridine-3,4-dicarboxylic acid, quinoline-3,4-dicarboxylic acid, 2-methyl-quinoline-3,4-dicarboxylic acid, 5,6,7,8-tetrachloro-2-methyl-quinoline-3,4-dicarboxylic acid, chloro- and bromo-2-ethyl-quinoline-3,4-dicarboxylic acid, , dimethyl- and trimethyl-quinoline-3,4-dicarboxylic acid, benzo-quinoline-3,4-dicarboxylic acid, pyridine-2,3-dicarboxylic acid, quinoline-2,3-dicarboxylic acid or anhydrides thereof.

The substituted naphthalene-1,8-diamines employed are commercially obtainable or can be prepared, for example, in accordance with DRP 122 475, DRP 108 166 and the like or analogously thereto. Suitable naphthalene-1,8-diamines are, for example:

1,8-naphthalenediamine, chloro-1,8-naphthalenediamines, dichloro-1,8-naphthalenediamines, bromo-1,8-naphthalenediamines, methyl-1,8-naphthalenediamines, dimethyl-1,8-naphthalenediamines, methyl-chloro-1,8-naphthalenediamines, methoxy-1,8-naphthalenediamines, ethoxy-1,8-naphthalenediamines, acetamino-1,8-naphthalenediamines and 4,5-dimethylenenaphthalene-1,8-diamine, wherein the substituents are preferably bonded in the 2-, 4-, 5- and 7-position of the naphthalene.

The dyestuffs of the formula (I) according to the invention can accordingly be prepared from unsubstituted and/or substituted educts, with a subsequent replacement of substituents, if appropriate. Replacement of substituents here is understood as meaning both replacement of a hydrogen or other ligands by a substituent, for example by means of chlorination, bromination, sulphonation, chlorosulphonation or nitration, and modification of substituents as described below by way of example.

Dyestuffs of the formula (I) in which X and/or Y represent an alkyl- or arylaminosulphonyl radical can also be prepared, as well as by the process first mentioned, from the corresponding dyestuffs of the formula (I) in which X and/or Y denote a chlorosulphonyl radical, with alkyl- or arylamines.

Dyestuffs according to the invention in which X and/or Y are an aryloxysulphonyl radical can also be obtained by reaction of the corresponding chlorosulphonyl dyestuffs with phenols or naphthols in the presence of a base, for example pyridine, triethylamine or alkali metal or alkaline earth metal carbonates, hydroxides or oxides.

Dyestuffs of the formula (I) in which X and/or Y represent alkyloxy or acyloxy can additionally be prepared by alkylation or acylation of the dyestuffs according to the invention in which X and/or Y denote a hydroxyl group.

Those dyestuffs of the formula (I) where X and/or Y are an optionally acylated or alkylated amino group can furthermore be obtained by reduction of the corresponding compounds in which X and/or Y represent a nitro group with customary reducing agents, for example iron, zinc, sodium sulphide, hydrogen and the like, and if appropriate subsequent acylation or alkylation. The acylation step can also be carried out in the course of the reduction by addition of an acylating agent, such as carboxylic acid anhydrides.

The dyestuffs according to the invention are outstandingly suitable for bulk dyeing plastics.

The invention therefore furthermore relates to a process for bulk dyeing plastics.

Bulk dyeing here is understood as meaning, in particular, a process in which the dyestuff is incorporated into the molten composition of plastic, for example with the aid of an extruder, or in which the dyestuff is already added to starting components for the preparation of the plastic, for example monomers before the polymerization.

Particularly preferred plastics are thermoplastics, for example vinyl polymers, cellulose esters, polyesters and polyamides.

Suitable vinyl polymers are polystyrene, styrene/acrylonitrile copolymers, styrene/butadiene copolymers, styrene/butadiene/acrylonitrile terpolymers, polymethyl methacrylate and the like.

Polyesters which are furthermore suitable are: polyalkylene terephthalates, such as polyethylene terephthalates, and polycarbonates.

Polystyrene, styrene copolymers, polycarbonates and polymethacrylate are preferred. Polystyrene is particularly preferred.

The high molecular weight compounds mentioned can be present individually or in mixtures, as plastic compositions or melts.

The dyestuffs according to the invention are brought into a finely divided form for use, it being possible, but not essential, for dispersing agents to be co-used. If the dyestuffs (I) are employed after the polymerization, they are mixed or ground with the granules of plastic in the dry state and this mixture is plasticized and homogenized, for example on mixing rolls or in screws. However, the dyestuffs can also be added to the molten composition and dispersed homogeneously by stirring. The material predyed in this manner is then further processed to mouldings in the customary manner, for example by spinning to bristles, filaments and the like or by extrusion or in the injection moulding process.

The invention therefore also relates to the plastics which have been dyed by one of the abovementioned processes. These include, for example, bristles, filaments, mouldings or films.

Since the dyestuffs of the formula (I) are resistant to polymerization catalysts, in particular peroxides, it is also possible to add the dyestuffs to the monomeric starting materials for the plastics and then to polymerize these materials in the presence of polymerization catalysts. For this, the dyestuffs are preferably dissolved in the monomeric components or mixed intimately with them.

The dyestuffs of the formula (I) are preferably employed for dyeing the polymers mentioned in amounts of 0.0001 to 1% by weight, in particular 0.01 to 0.5% by weight, based on the amount of polymer.

By addition of pigments which are insoluble in the polymers, such as, for example, titanium dioxide, corresponding useful opaque dyeings can be obtained.

Titanium dioxide can be used in an amount of 0.01 to 10% by weight, preferably 0.1 to 5% by weight, based on the amount of polymer.

Transparent or opaque brilliant, orange to violet dyeings having a good heat stability and good fastness to light and weathering are obtained by the process according to the invention.

Mixtures of different dyestuffs of the formula (I) and/or mixtures of dyestuffs of the formula (I) with other dyestuffs and/or inorganic or organic pigments can also be employed in the process according to the invention.

The invention is explained by, but not limited to, the following examples, in which the parts are stated as parts by weight and percentage data denote percentages by weight (% by weight).

EXAMPLE 1

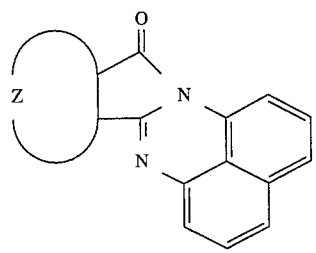

(Z=radical to complete a 2,6-dimethyl-3,4-pyridinylene ring)

A) Preparation

A mixture of 4.8 g of naphthalene-1,8-diamine, 4.8 g of 2,6-dimethyl-pyridine-3,4-dicarboxylic acid and 35 g of phenol is heated at 150° C. under nitrogen for 1 hour. It is then cooled to 80° C. and diluted with 30 ml of methanol, and, after cooling, the precipitate formed is filtered off with suction. After the precipitate has been washed with methanol and dried, 6.0 g of the dyestuff of the above formula are obtained.

B) Dyeing Examples

Example a)

100 parts of polystyrene granules and 0.02 part of a dyestuff of the above formula are mixed intensively in a drum mixer for 15 minutes. The granules which have been coloured in the dry state are processed on a screw injection moulding machine at 240° C. Transparent, red sheets of very good fastness to light are obtained. Instead of polystyrene polymer, it is also possible to use butadiene/acrylonitrile copolymers, such as styrene/butadiene/acrylonitrile. If 0.5 part of titanium dioxide is additionally added, deep opaque dyeings are obtained.

Example b)

0.015 part of the dyestuff from Example A) and 100 parts of polymethyl methacrylate are mixed in the dry state and homogenized on a 1-screw extruder at 230° C. The material emerging from the extruder as a strand is granulated. The granules can then be compression moulded to shapes. A plastic which has been dyed a transparent red and has good fastness to light and weathering is obtained.

Example c)

100 parts of a commercially available polycarbonate are mixed in the dry state in the form of granules with 0.03 part of the dyestuff from Example A). The granules thus dusted are homogenized on a 2-screw extruder at 290° C. A transparent red dyeing of good fastness to light is obtained. The dyed polycarbonate is discharged from the extruder as a strand and processed to granules. The granules can be processed by customary methods.

If the procedure is as described above, but 1% of titanium dioxide is added, a red opaque dyeing is obtained.

Example d)

0.04 part of the dyestuff from Example A) is mixed in the dry state with 100 parts of styrene/acrylonitrile copolymer, the mixture is homogenized in a 2-screw extruder at 190° C. and granulated and the granules are then compression moulded to shapes in the customary manner. A transparently red plastic of good fastness to light is obtained.

Example e)

0.025 part of the dyestuff from Example A) is mixed with 100 parts of polyethylene terephthalate of a transparent type and the mixture is homogenized in a 2-screw extruder at 280° C. A transparent, red dyeing of good fastness to light is obtained. After subsequent granulation, the coloured plastic can be processed by the customary methods of thermoplastic shaping. If the procedure is carried out with the addition of 1% of titanium dioxide, an opaque dyeing is obtained.

Example f)

0.05 part of tert-dodecylmercaptan and 0.05 part of the dyestuff from Example A) are dissolved in 98.9 parts of styrene. This solution is dispersed in a solution of 200 parts of desalinated water, 0.3 part of partly hydrolysed polyvinyl acetate (for example Mowiol® 50/88 from Hoechst) and 0.05 part of dodecylbenzenesulphonate. After addition of 0.1 part of dibenzoyl peroxide in 1 part of styrene, the dispersion is heated to 80° C., while stirring vigorously, and the polymerization is started. Using the following polymerization conditions: 4 hours at 80° C., 2 hours at 90° C., 3 hours at 110° C., 2 hours at 130° C., the polymer is obtained in a yield of 98% of theory. The polymer is obtained in the form of beads, which have a diameter of 0.1 to 1.5 mm ($D_{50}$ value), depending on the stirring conditions. The polymer is separated from the serum by filtration and dried at 110° C. to a residual moisture content of 0.5%. After melting in a mixing unit (hot mill), 0.5% of zinc stearate and 0.2% of Ionol are admixed and the polymer is granulated.

The polymer can be processed to red, transparent mouldings by the customary methods of thermoplastic shaping, for example in the injection moulding process.

Example g)

0.2 part of tert-dodecylmercaptan and 0.01 part of the dyestuff from Example A) are dissolved in 74.8 parts of styrene and 25 parts of acrylonitrile, and this solution is then dispersed in a solution of 200 parts of completely desalinated water and 0.2 parts of a copolymer of styrene and maleic anhydride neutralized with sodium hydroxide. After addition of 0.1 part of dibenzoyl peroxide dissolved in one part of styrene, the dispersion is heated to 80° C., while stirring vigorously, and the polymerization is started. After the polymerization as in Example f), the polymer is also worked up in the same manner as described in that Example. 0.5% of zinc stearate as a lubricant and 0.5% of Ionol as an anti-aging agent are incorporated on the hot mill. The granulated polymer can be injection moulded to transparent red mouldings.

Example h)

A solution of 99.95 parts of styrene, 0.04 part of the dyestuff from Example A) and 0.01 part of di-tert-butyl peroxide is introduced into a continuously working preliminary reactor operated with an overflow, and subjected to prepolymerization at a temperature of 75° C. The prepolymerized solution emerging from the preliminary reactor (polystyrene content 20%) is introduced into a 2-shaft screw unit. The two shafts run in opposite directions at 20 rpm. The four heatable and coolable segments of the screw machine are kept at 110° C., 130° C., 160° C., 180° C. in the sequence product intake-product discharge. The polymer leaves the screw reactor with a solids concentration of 80%. 3 parts by weight of Ionol and 5 parts by weight of octyl alcohol per 1000 parts by weight of polymer solution are metered into a downstream extruder and the polymer is degassed and then granulated. The granules which have been dyed red can be processed to mouldings.

Example i)

0.02 part of the dyestuff from Example A) is dissolved in 74.97 parts of styrene and 25 parts of acrylonitrile or methacrylonitrile. After addition of 0.01 part of di-tert-butyl peroxide, the solution thus obtained is introduced into a continuously working preliminary reactor operated with an overflow. The polymerization and working up are carried out as described in Example h). The transparent, red granules can be further processed to profiles and sheets by the customary methods of processing of thermoplastic compositions.

Example k)

0.03 part of the dyestuff from Example A) is dissolved in 99.97 parts of methyl methacrylate.

After addition of 0.1. part of dibenzoyl peroxide, the solution is heated to 120° C. and the polymerization is started. After 30 minutes, the prepolymerized methyl methacrylate is polymerized completely between two glass plates at 80° C. for ten hours. Red, transparent polymethyl methacrylate sheets are obtained.

Example l)

100 parts of polyamide 6 chips obtained by polymerization of ε-caprolactam are intimately mixed with 0.05 part of the dyestuff from Example A) in a mechanical shaker. The powdered chips thus obtained are melted at 260° C. in an extruder, the resulting melt is forced through a single-hole die of 0.5 mm diameter and the emerging filament is drawn off at a rate of about 25 m/minute. The filament can be stretched four-fold in hot water. A filament which has been dyed a transparent red and has excellent fastness to light is obtained. If an opaque dyeing is required, 0.5 part of titanium dioxide is additionally added.

The residence time in the extruder can be up to 30 minutes without impairment of the colour shade.

EXAMPLE 2

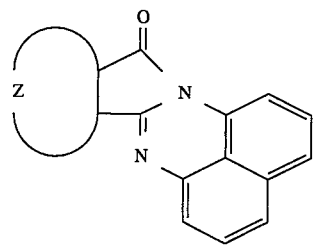

(Z=radical to complete a 3,4-pyridinylene ring)

4.8 g of naphthalene-1,8-diamine and 5.0 g of pyridine-3,4-dicarboxylic acid are dissolved in 50 ml of pyridine at 70° C., and 10 ml of acetic anhydride are then added, the temperature rising to 120° C. The mixture is heated under reflux for a further 30 minutes and then allowed to cool. The precipitate is filtered off with suction, washed first with a little pyridine and then with methanol and finally dried.

Yield: 5.5 g

For purification, the dyestuff can be recrystallized from toluene.

In plastics dyed analogously to Dyeing Examples B) in Example 1, the dyestuff gives yellowish red dyeings with a high level of fastness.

EXAMPLE 3

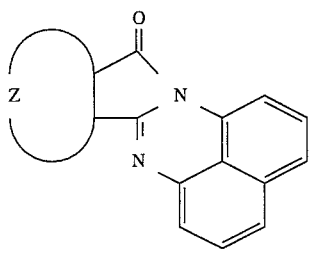

(Z=radical to complete a 2,5,6-trimethyl-3,4-pyridinylene ring)

A mixture of 3.8 g of 2,5,6-trimethylpyridine-3,4-dicarboxylic acid anhydride, 3.1 g of naphthalene-1,8-diamine and 20 g of phenol is heated to 150° C. under nitrogen for 30 minutes. It is then cooled to 80° C. and diluted with 10 ml of methanol and the precipitate which has formed is filtered off with suction at room temperature. After the precipitate has been washed with methanol and dried, 4.8 g of the product of the above formula, which dyes plastics in reddish orange, highly fast colour shades according to Dyeing Examples B) from Example 1, are obtained.

EXAMPLE 4

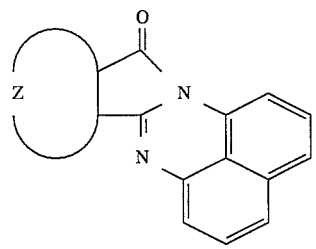

(Z=radical to complete a 6-phenyl -3,4-pyridinylene ring)

A mixture of 20 g of phenol, 3.1 g of naphthalene-1,8-diamine and 4.9 g of 6-phenylpyridine-3,4-dicarboxylic acid is heated to 150° C. in the course of 30 minutes and kept at this temperature for 90 minutes, the water of reaction being distilled off. The dyestuff is then precipitated with 10 ml of methanol at 60°–80° C., filtered off with suction at room temperature and washed with methanol.

Yield: 1.4 g; for purification, the dyestuff can be recrystallized from toluene.

In plastics dyed analogously to Dyeing Examples B) in Example 1, the dyestuff gives red dyeings with a high level of fastness.

EXAMPLE 5

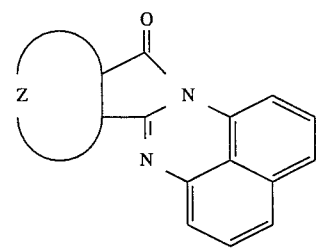

(Z=radical to complete 2-methyl-6-phenyl-3,4-pyridinylene ring)

7.9 g of naphthalene-1,8-diamine are initially introduced into phenol (50 g) at 50° C., and 12.9 g of 2-methyl-6-phenylpyridine-3,4-dicarboxylic acid are then added. Thereafter, the mixture is heated to 150° C. in the course of 30 minutes and the temperature is maintained for a further 30 minutes. The mixture is then cooled to 100° C., 25 ml of methanol are added dropwise and the mixture is then cooled to room temperature. The precipitate is washed with methanol and hot water and dried.

Yield: 16.5 g

The dyestuff dyes plastics according to Dyeing Examples B) from Example 1 in highly fast red colour shades.

EXAMPLE 6

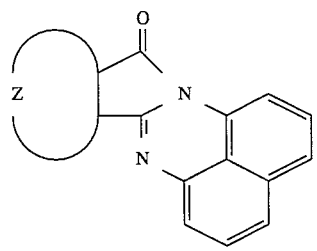

(Z=radical to complete a 2-methyl-3,4-quinolinylene ring)

A mixture of 6.0 g of quinoline-3,4-dicarboxylic acid anhydride, 4.8 g of naphthalene-1,8-diamine and 30 g of phenol is heated at 135° C. under nitrogen for 1 hour. The product is then precipitated with 25 ml of methanol at 80° C. and the precipitate is filtered off with suction at 40° C. After the precipitate has been washed with methanol and dried in vacuo, 7.8 g of the dyestuff of the above formula are obtained as a mixture of the two isomers.

In plastics dyed analogously to Dyeing Examples B) from Example 1, the dyestuff gives red-violet dyeings with good fastness properties.

EXAMPLE 7

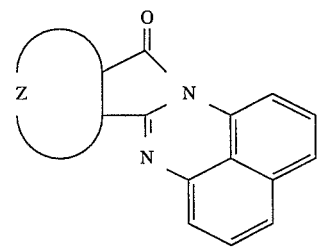

(Z=radical to complete a 2,3-pyridinylene ring)

15.8 parts of 1,8-diamino-naphthalene are dissolved in 70 parts by volume of propionic acid under a nitrogen atmosphere. The mixture is heated to 130° C. and 14.9 parts of pyridine-2,3-dicarboxylic acid anhydride are rapidly added dropwise, while stirring. The reaction mixture is then stirred at 130° C. for 5 hours. After cooling, the reaction mixture which has separated out is filtered off with suction and washed with 50 parts by volume of methanol and 100 parts by volume of water. After drying at 50° C. in vacuo, 12.2 parts of the amorphous isomer mixture, which can be crystallized in orange bars from about 160 parts by volume of dimethylformamide, are obtained.

The dyestuff dyes plastics according to Dyeing Example B) from Example 1 in highly fast orange colour shades.

We claim:
1. Dyestuffs of the formula

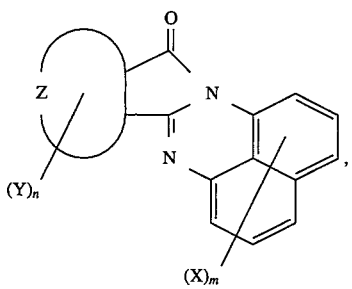

wherein

Z denotes a radical to complete a 3,4- or 2,3-pyridinylene, a 4,5-pyrimidinylene, a 3,4- or 4,5-pyridazinylene or a 2,3-pyrazinylene system, X is alkyl, halogen, nitro, chlorosulphonyl, aryloxysulphonyl, hydroxyl, alkoxy, acyloxy, an aminosulphonyl which is unsubstituted or substituted by alkyl or aryl, or a fused-on cycloaliphatic ring, Y is alkyl, aryl, halogen, nitro, hydroxyl, alkoxy, acyloxy, aryloxysulphonyl, chlorosulphonyl, an amino group which is unsubstituted or substituted by acyl or alkyl, an aminosulphonyl radical which is unsubstituted or substituted by alkyl or aryl, or a fused-on cycloaliphatic or aromatic ring, m is a number between 0 and 6, n is a number between 0 and 3 and for m >1

X can in each case have different or identical meanings as mentioned above, and for n>1

Y can in each case have different or identical meanings as mentioned above.

2. Dyestuffs according to claim 1, wherein Z denotes a radical to complete a 3,4-pyridinylene system.

3. Dyestuffs according to claim 1, wherein

X represents chlorine, bromine, $-NO_2$, $-OCH_3$, $-OCH_2(C_6H_5)$, chlorosulphonyl, $-OH$, $-SO_2O(C_6H_5)$, $-SO_2N(CH_3)_2$, $-SO_2NHCH_3$, methyl, ethyl, n-propyl, isopropyl, n-butyl, iso-butyl, sec-butyl, tert-butyl or a cycloaliphatic 5- or 6-membered ring, Y is methyl, ethyl, n-propyl, isopropyl, n-butyl, iso-butyl, sec-butyl, tert-butyl, a phenyl which is unsubstituted or substituted by $C_1$–$C_6$-alkoxy, $C_1$–$C_6$-alkyl, Cl, Br or F, a fused-on cycloaliphatic 5-, 6- or 7-membered ring or a fused-on benzo ring, m is a number between 0 and 4 and n is a number between 0 and 3.

4. Dyestuffs of the formula (I) according to claim 1, wherein m is zero.

5. Process for the preparation of the dyestuffs (I) according to claim 1, wherein dicarboxylic acids or functional derivatives thereof of the formula (II)

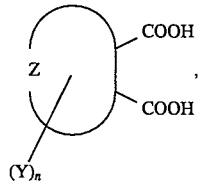

wherein Z, Y and n have the meanings given under claim 1, are reacted with naphthalene-1,8-diamines of the formula (III)

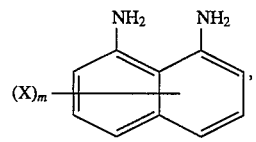

in which X and m have the meaning given under claim 1, in the melt or in a solvent at temperatures of between 20° C. and 220° C., if appropriate in the presence of an acid catalyst and/or under pressure.

6. Process according to claim 5, wherein dicarboxylic acids of the formula (II) or anhydrides thereof wherein Z denotes a radical to complete a 3,4-pyridinylene system are used.

7. Process for bulk dyeing plastics, which comprises applying thereto a dyestuff according to claim 1.

8. Process according to claim 7, wherein the plastic is a thermoplastic.

9. Process according to claim 7, wherein the plastic to be dyed is a vinyl polymer or a polyester.

10. Plastics dyed according to claim 7.

* * * * *

UNITED STATES PATENT AND TRADEMARK OFFICE
CERTIFICATE OF CORRECTION

PATENT NO.   : 5,621,027
DATED        : April 15, 1997
INVENTOR(S)  : Roschger, et al.

It is certified that error appears in the above-indentified patent and that said Letters Patent is hereby corrected as shown below:

Col. 11, line 18    Delete " system " and substitute
                    -- ring --

Signed and Sealed this

Fifth Day of August, 1997

*Attest:*

BRUCE LEHMAN

*Attesting Officer*          *Commissioner of Patents and Trademarks*